(12) United States Patent
Aflatoon

(10) Patent No.: US 8,790,373 B2
(45) Date of Patent: Jul. 29, 2014

(54) DYNAMIC INTER-SPINOUS PROCESS SPACER

(76) Inventor: Kamran Aflatoon, Corona del Mar, CA (US)

( * ) Notice: Subject to any disclaimer, the term of this patent is extended or adjusted under 35 U.S.C. 154(b) by 149 days.

(21) Appl. No.: 13/184,150

(22) Filed: Jul. 15, 2011

(65) Prior Publication Data

US 2012/0016419 A1    Jan. 19, 2012

Related U.S. Application Data

(60) Provisional application No. 61/364,473, filed on Jul. 15, 2010.

(51) Int. Cl.
*A61B 17/70* (2006.01)

(52) U.S. Cl.
CPC .................. *A61B 17/7067* (2013.01)
USPC .......................... 606/249; 606/248

(58) Field of Classification Search
CPC ........... A61B 17/7062; A61B 17/7065; A61B 17/7067; A61B 2017/025; A61B 2017/0256; A61F 2/44; A61F 2/4405; A61F 2/441; A61F 2002/44; A61F 2002/30581
USPC .......................... 606/248–249, 291; 623/17.12
See application file for complete search history.

(56) References Cited

U.S. PATENT DOCUMENTS

| | | | |
|---|---|---|---|
| 2005/0070904 A1* | 3/2005 | Gerlach et al. | 606/69 |
| 2006/0241601 A1* | 10/2006 | Trautwein et al. | 606/61 |
| 2007/0276368 A1* | 11/2007 | Trieu et al. | 606/61 |
| 2009/0216274 A1* | 8/2009 | Morancy-Meister et al. | 606/247 |
| 2010/0249841 A1* | 9/2010 | Trieu et al. | 606/249 |
| 2011/0295370 A1* | 12/2011 | Suh et al. | 623/17.12 |

* cited by examiner

*Primary Examiner* — Eduardo C. Roberts
*Assistant Examiner* — Julianna N Harvey
(74) *Attorney, Agent, or Firm* — Ober, Kaler, Grimes & Shriver; Royal W. Craig; Christopher F. Lonegro

(57) ABSTRACT

A vertebral spacer includes an expandable member having a self sealing percutaneous fluid access port and engaged to an anchor member that is secured the vertebrae. The anchor member may be an arcuate channel mechanically secured to adjacent spinous processes by bone screws through slots in the legs of the channel. The port allows for adding or removing fluid from the expandable member in order to adjust the volume thereof and thus the interspinous process spacing. Subsequent to initial expansion, the volume of the expandable member may be increased or decreased by using a needle to add or remove fluid from the expandable member via the port. The fluid may be a liquid, gel, or a viscous polymer and may remain in a liquid state or harden to a viscoelastic state.

11 Claims, 6 Drawing Sheets

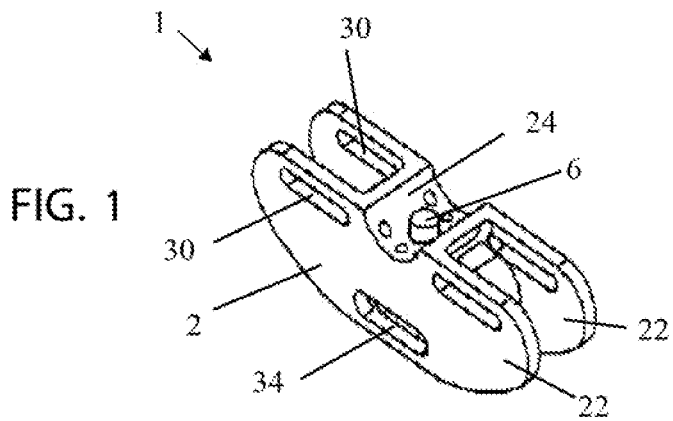
FIG. 1
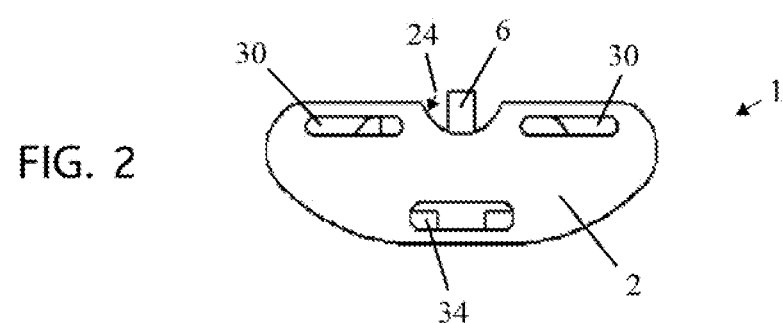
FIG. 2
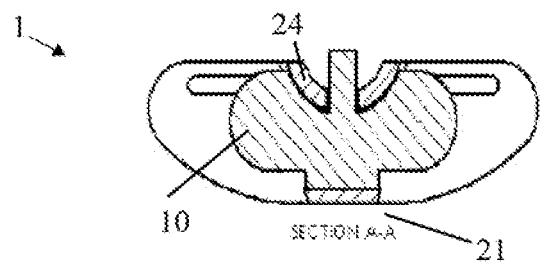
FIG. 3
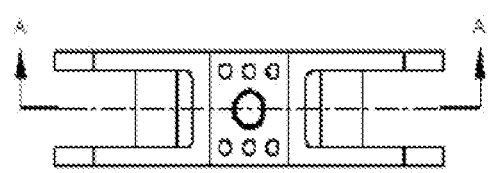

DYNAMIC INTER-SPINOUS PROCESS SPACER

CROSS-REFERENCE TO RELATED APPLICATIONS

The present application claims priority to U.S. provisional patent application Ser. No. 61/364,473 filed Jul. 15, 2010 which is incorporated herein by reference.

BACKGROUND OF THE INVENTION

1. Field of the Invention

The present invention relates generally to devices and methods for treating spinal disorders and more specifically to a variable volume inter-spinous process spacer that can be implanted in a minimally invasive manner.

2. Description of the Background

Degeneration of the intervertebral discs and the concomitant instability and translocation of the vertebra (spondylolisthesis) is a common cause of back pain and may result from a variety of problems including congenital deformity, age related degeneration, osteoporosis, tumor and disc herniation as a result of trauma. Disc degeneration, for whatever reason, results in compression of the spinal nerve roots (stenosis) resulting in pain. Other causes of stenosis include changes in ligament morphology, vertebral bone spurs in or near the spinal canal and degeneration of the facet joints. Palliative care such as physical therapy, nonsteroidal anti-inflammatories (NSAIDS) and epidural steroid injections are often successful used in the treatment of mild cases but more extreme or degenerative cases may require a surgical approach to stabilize the spine and relieve pressure.

The standard surgical treatments for symptomatic degenerative spondylolisthesis and spinal stenosis have, for many years, included decompressive laminectomy in which the lamina of one or more vertebrae is removed to enlarge the space available and relieve pressure on the spinal cord or spinal nerve roots. Lumbar decompression and spinal fusion to decompress the nerve roots and/or spinal cord and to stabilize the spine are also frequently employed. However, many patients suffering from degenerative conditions have comorbidities that make them less than perfect surgical candidates. As a result, several different methods have more recently been devised as alternative treatments for degenerative spondylolisthesis and spinal stenosis.

One such alternative treatment is interspinous process distraction (IPD) which is also known as interspinous distraction or posterior spinal distraction. During IPD the spinous processes are mechanically pushed apart or distracted to relieve pressure on the spinal cord and/or nerve roots that is caused by the spondylolisthesis and spinal stenosis. An inter-spinous process spacer may be inserted into and retained in the interspinous process space created by the procedure to maintain the modified geometry.

The overall goals of traditional lumbar decompression with or without lumbar fusion and IPD are the same in that they both aim to relieve lower extremity neuropathy and claudication and may alleviate low back pain. IPD, however, offers advantages over the standard treatment in that it is not as invasive as laminectomy or lumbar decompression and spinal fusion leading to shorter surgery times and shorter hospital stays and rehabilitation periods. IPD can further be accomplished under local anesthesia, preserves more local bone and soft tissue, has a reduced risk of epidural scarring and cerebrospinal fluid leakage and is reversible so as not to limit any future treatment options. The potential complications of IPD include dislodgement of the spacer, incorrect positioning or sizing of the spacer, fracture of the spinous process, foreign body reaction to the spacer (e.g., allergic reaction to titanium alloy) and mechanical failure of the spacer.

It would, therefore, be an improvement in this art to provide an interspinous process spacer that can be implanted in a minimally invasive procedure so as to retain the advantages of existing methods but that avoids the limitations of previous spacers. Such a spacer would be capable of being securely retained in place, would maintain the greatest possible contact area with the spinous processes so as to distribute loading forces and reduce the chance of fracture, would be of a robust design that is unlikely to fail mechanically and constructed of materials that are unlikely to cause allergic reactions. Such a spacer would further be capable of being sized and positioned during the implantation procedure and of being resized by percutaneous methods after implantation for an extended or indefinite period.

SUMMARY OF THE INVENTION

Accordingly, there is provided an interspinous process spacer and method of implantation for distraction of the vertebra including an expandable member, a self sealing percutaneous access port in fluid engagement with the expandable member and an anchor member secured to and in fluid engagement with said tubular member. The anchor member may be an arcuate channel mechanically secured to adjacent spinous process by bone screws through a plurality of slots in the legs of the channel. The port allows for adding or removing fluid from the one or more chambers or envelopes of the expandable member in order to adjust the volume of the expandable member and thus the interspinous process spacing. Subsequent to initial implantation and expansion the volume of the expandable member may be increased or decreased in a non-surgical in-office procedure in which a needle is used to add or remove fluid from the expandable member via the port and tubular member. The flowable material/fluid may be a liquid such as saline, gel such as silicone, or a viscous polymer and my further remain in a liquid state or harden to a viscoelastic state with or without additional intervention.

The foregoing objects, features and attendant benefits of this invention will, in part, be pointed out with particularity and will become more readily appreciated as the same become better understood by reference to the following detailed description of a preferred embodiment and certain modifications thereof when taken in conjunction with the accompanying drawings.

BRIEF DESCRIPTION OF THE DRAWINGS

In the drawings:

FIG. 1 is a perspective view of an interspinous process spacer according to the present invention.

FIG. 2 is a side view of an interspinous process spacer according to the present invention.

FIG. 3 is a section view of an interspinous process spacer according to the present invention without the balloon assembly in place.

DETAILED DESCRIPTION OF THE PREFERRED EMBODIMENTS

Figure 4:
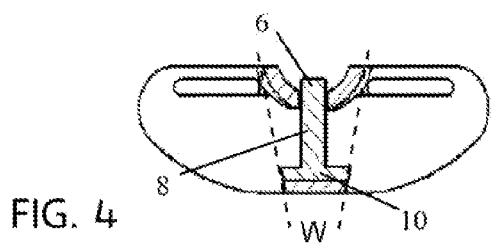
FIG. 4 is a section view of an interspinous process spacer according to the present invention with the balloon, assembly in place but deflated.

With collective reference to FIGS. 1 through 8, an interspinous process spacer 1 having an anchor member 2 is provided. In the depicted, preferred embodiment the anchor member 2 has a generally C-channel cross section have opposing legs (or flanges) 22 of preferably equal length extending from a base member (or web) 24. The legs 22 are preferably orthogonal to the base member 24 but may be splayed outward slightly from the depicted 90° angle to accommodate vertebral physiology of the spinous processes in certain regions of the human (or other) spine. The term "orthogonal" as used herein is inclusive of such splayed angles (i.e. non-90° angles). The legs 22 are preferably splayed not more than 15° each on either side so as to maintain sufficient contact with the bone while not interfering with adjacent tissue structures and are preferably splayed from 5° to 15° and even more preferably 5° to 10°. Some resilience in the leg construction may also be provided and desirable to further accommodate vertebral physiology. However, resilient bending or deformation of the legs 22 will be limited by a bridging member 21 that joins at least a portion of the legs their distal ends. Resilient bending of the legs must be limited (but not necessarily eliminated) because the legs serve to not only secure the spacer in place but also to support and contain the expandable/collapsible member 10.

Figure 8:
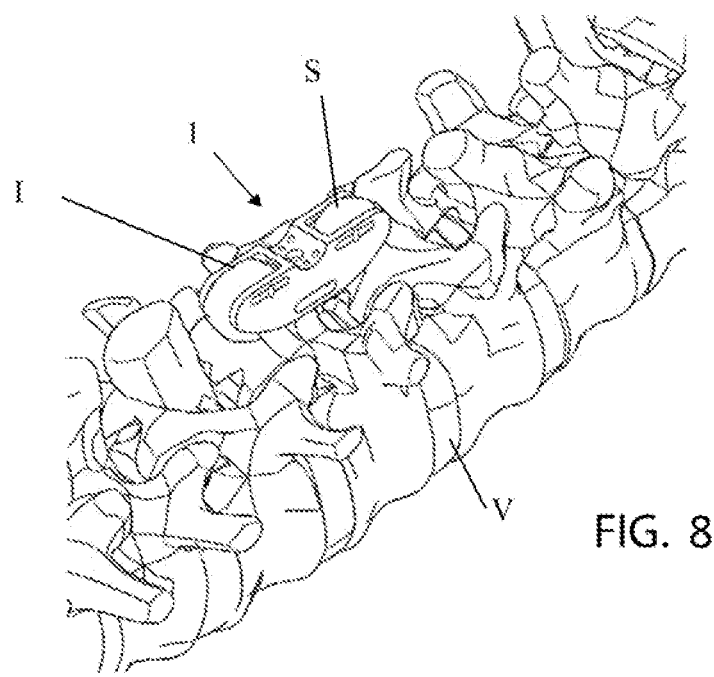
FIG. 8 is an anterio-lateral perspective view of an interspinous process spacer according to the present invention in-situ.
Figure 14:
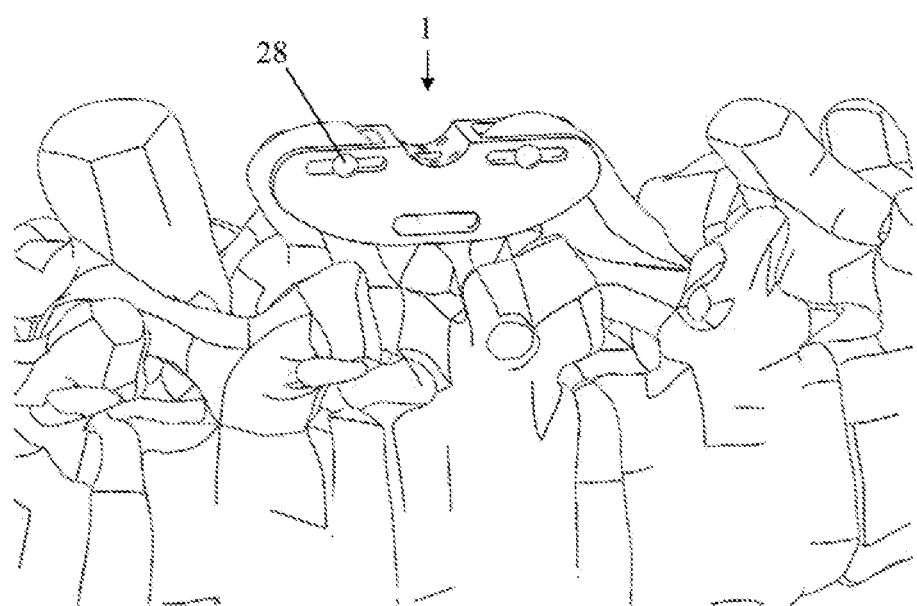
FIG. 14 is an lateral perspective view of an interspinous process spacer according to the present invention in-situ.
Figure 9:
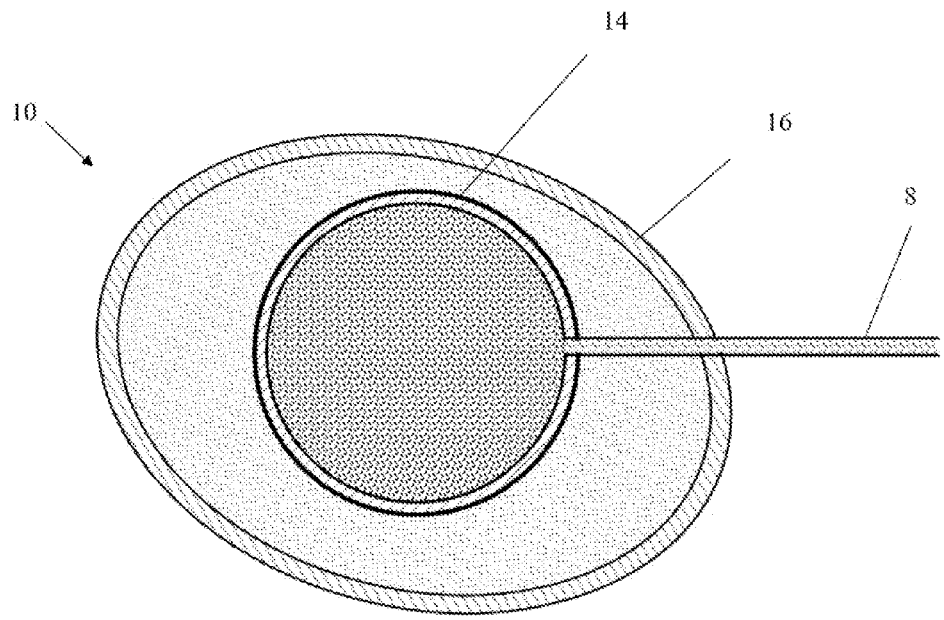
FIG. 9 is a schematic partial section though the expandable/collapsible member of an interspinous process space according to an alternate embodiment of the present invention.
Figure 10:
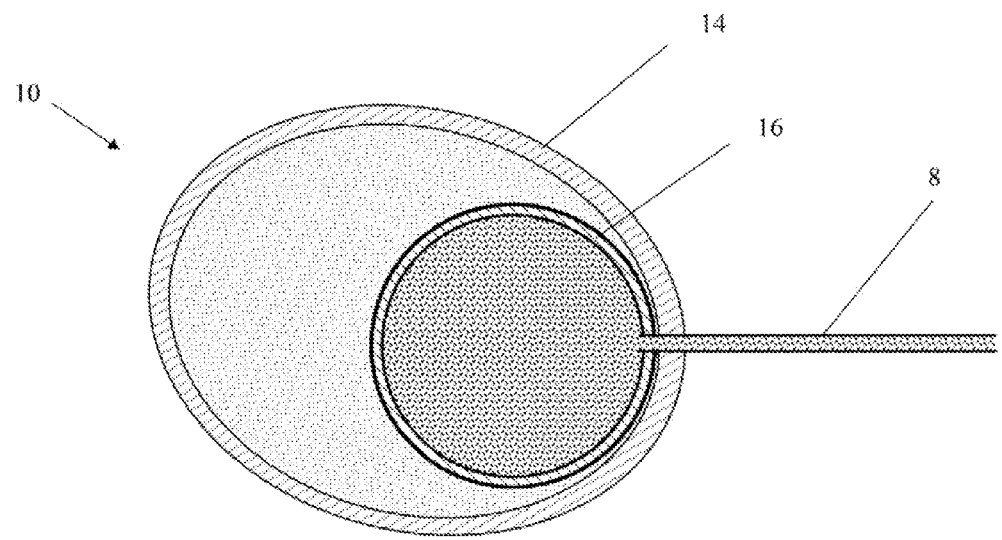
FIG. 10 is a schematic partial section though the expandable/collapsible member of an interspinous process space according to an alternate embodiment of the present invention.
Figure 11:
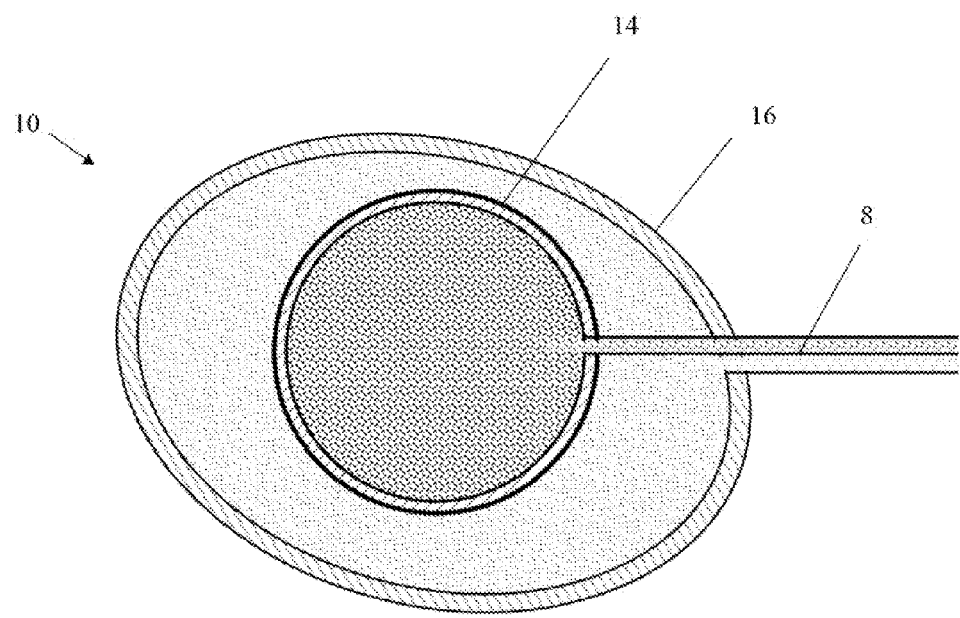
FIG. 11 is a schematic partial section though the expandable/collapsible member of an interspinous process space according to an alternate embodiment of the present invention.
Figure 12:
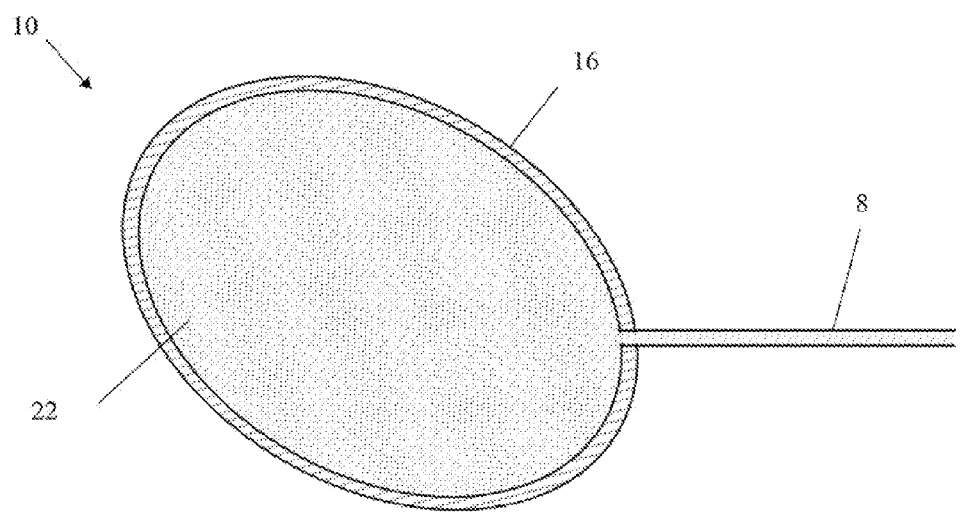
FIG. 12 is a schematic partial section though the expandable/collapsible member of an interspinous process space according to an alternate embodiment of the present invention.
Figure 13:
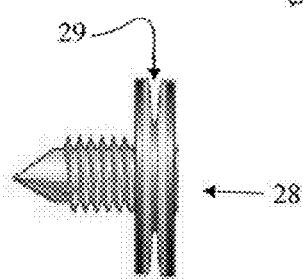
FIG. 13 is a bone screw according to the present invention.
Figure 16:
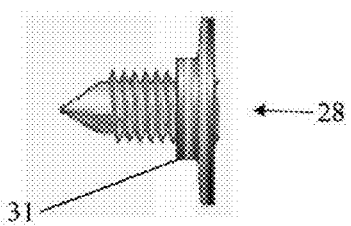
FIG. 16 is an alternative bone screw according to the present invention.

After being positioned in-situ as, for example, depicted in FIG. 8, a series of bone screws 28 (See. FIGS. 13, 14) are driven through slots 30 in each of the legs 22 of the anchor member 2 and into the bone to secure the spacer in place. The bone screws 28 also serve to limit additional resilient splaying of the legs 22 after an initial deformation on insertion but are driven into the bone deep enough to be securely fastened but not so far that the screw head pins the legs 22 to the bone. Rather, the head of the screw 38 is held off of the bone surface in order to permit movement of the screws within the elongate slots 30 so as to permit and accommodate some movement of the inferior (I) or superior (S) spinous process of the vertebral joint (V). With reference to FIG. 13, a bone screw 28 having a preformed annular channel 29 about its head may be used to prevent over tightening of the screws 28 into the bone and thereby preventing sliding of the screws in the slots 30. The inner surface of channel 29 may be coated with a biocompatible low friction coating such as Teflon® or Nylon to facilitate movement. In another alternate embodiment, a stop or spacer in the form of an unthreaded portion 31 of the screw having an increased diameter as compared to the threaded portion is provided just below the head of the screw such that the stop engages the bone surface within the slot and holds the head slightly above the bone surface.

Because of the close proximity of screws 28 entering the spinous process from each of the opposing legs, care should be taken to avoid interference of the screws with one another as for example by offsetting the position of the screws relative to one another. In certain embodiments the slots 30 may also be offset. In certain other embodiments the screws 28 on opposing sides may be replaced by a single screw post joined through the spinous process.

The anchor member 2 is preferably arcuate in form so as to be adapted for insertion into the inter-spinous process space and to be sufficiently strong and rigid and yet resilient without being cumbersome or oversized or interfering with adjacent tissue structures. The anchor member is preferably from 10 mm to 20 mm and more preferably is 15 mm in length, length being the direction along the longitudinal axis of the spine when the spacer 1 is in-situ. The bridging member 21 is shorter in length than the arcuate member, from 5 to 15 mm and preferably 10 mm. The bridging member 21 is further preferably tapered or sympathetically curved with the base member 24 such that taken together the base member and the bridging member form a wedge W (See FIG. 4) that facilitates insertion of the spacer into the inter-spinous process space without over stressing the bones. The curved or arcuate form of the base member 24 also serves the dual purpose of providing an initial distraction on insertion prior to inflation of the expandable/collapsible member 10 and of bolstering the expandable/collapsible member. In a preferred embodiment the base member 24 also serves to locate and support a fill port 6 for adding or removing material from the expandable/collapsible member 10 as will be described. The anchor member 2 may be constructed of implantable/bio compatible materials having the requisite strength and stiffness properties including metals such as titanium and stainless steel or polymers such as Polyether ether ketone (PEEK). An access opening 34 may preferably be provided through one or both legs 22 of the spacer 1 to afford access to the expandable/collapsible member 10 and to permit subsequent replacement of the expandable/collapsible member in a subsequent surgical procedure without the need to remove the anchor member 2.

In some embodiments, the anchor member 2 of the representative spacer 1 is further provided with a tubular member 8. The tubular member 8 may be flexible or semi rigid and is preferably formed of an implantable polymeric compound such a urethane, polyether urethane, silicone, thermoplastic silicone-urethane copolymers, polycarbonate urethane and others and may be reinforced or unreinforced. The tubular member 8 may further be multi-lumen tubing as further described below. Where semi-rigid materials are used the tubing is preferably kink-resistance yet plastically deformable such that the tubing may be bent, shaped or otherwise articulated relative to the anchor member 2 without collapse of the lumen(s) and capable of retaining its articulated shape when released. Where flexible materials in the nature of silicone medical tubing are utilized for tubular member 8, plastic deformation for articulation is not required and it is sufficient that the tubing resist collapse when bending or flexing.

Figure 5:
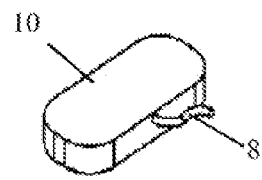
FIG. 5 is a perspective view of the balloon assembly deflated.
Figure 6A:
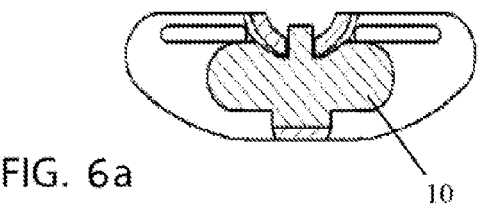
FIG. 6a is a section view of an interspinous process spacer according to the present invention with the balloon assembly in place and inflated to a first level.
Figure 6B:
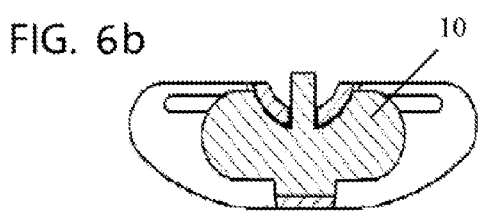
FIG. 6b is a section view of an interspinous process spacer according to the present invention with the balloon assembly in place and inflated to a second level.
Figure 7:
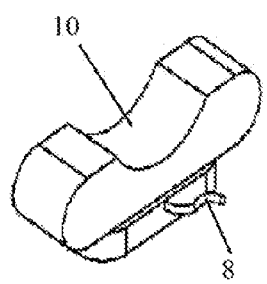
FIG. 7 is a perspective view of the balloon assembly inflated.
Figure 15:
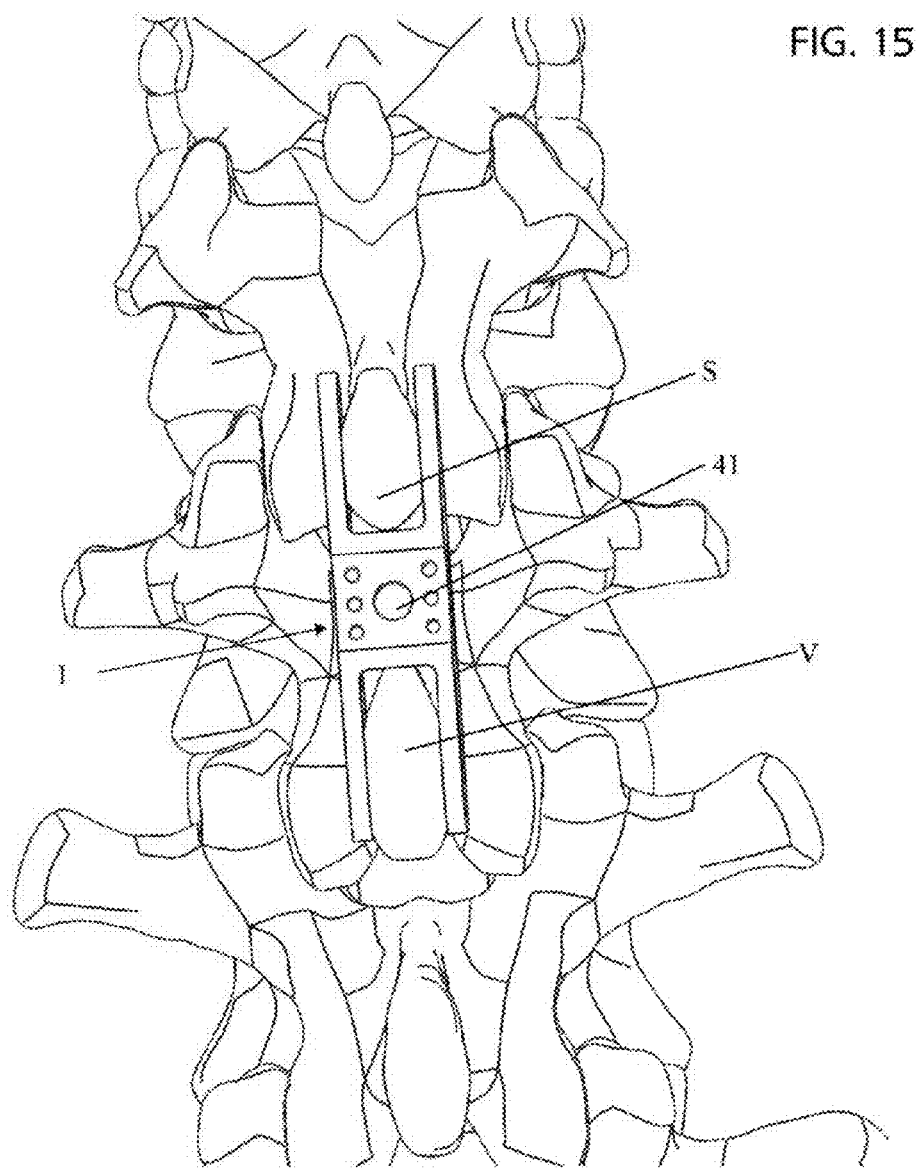
FIG. 15 is an anterior perspective view of an interspinous process spacer according to the present invention in-situ

The distal end of tubular member 8 terminates at a sealingly connected flexible, expandable/collapsible member 10 in the nature of a container or balloon having flexible, and preferably elastic walls. The expandable/collapsible member 10 is positioned within the channel of the anchoring member and is preferably affixed on the inside surface of the bridging member 21. The bridging member is generally sized to be as small as possible (typically approximately 10 mm) while still supporting the expandable/collapsible member 10 and may be a single post although it is preferably a limited curved or flat planar area as herein depicted. As best seen in FIGS. 4 and 5, the expandable/collapsible member 10 is provided, in its pre-implantation condition, in a collapsed and evacuated state so as to take up a minimum volume. The walls of the outer envelope 16 of the expandable/collapsible member 10 are preferably constructed of Kevlar, polypropylene, urethane, silicone elastomers such as polydimethylsiloxane or polymethylvinylsiloxane, polymethyl methacrylate, polycarbonate and copolymers thereof or other impermeable, implantable polymers as will be apparent to those skilled in the art. The expandable/collapsible member is, when inflated, preferably generally tubular in form with its longitudinal axis generally parallel to that of the anchor member 2 and fills the "taco shell" form of the anchor member 2. As seen in FIGS. 6 and 7, the inflated expandable/collapsible member 10 is preferably kidney shaped, or is directed into a kidney shape by engagement with the inside, curved surface of the base member 24), to provide upper and lower lobes to engage the superior and inferior spinous processes, respectively. Engagement of expandable/collapsible member 10 with the base member 24 and the inside surfaces of the legs 22 bolsters, contains and supports the member under the compressive loads of the superior and inferior spinous processes and prevents later migration or rotation.

Where present, the tubular member 8 is further in sealed fluid contact with a fill port 6 provided in or on a surface of the anchor member 2 (or remotely elsewhere on the spine) and preferably positioned within the arc of the base member 24 for ease of location. The fill port 6 may be any of a variety of known ports for subcutaneous implantation and subsequent percutaneous access to add or remove material from the expandable/collapsible member 10 as further described below. Fill port 6 is self sealing and suitable for multiple engagement in which material is added or removed from the expandable/collapsible member 10 via the tubular member 8. With reference to FIG. 15, one or more perforations 42 through the base member 24 may be provided to in which to mount the fill port 6 and route the tubular member 8.

With reference to FIGS. 9-12, the expandable/collapsible member 10 may be further comprised of an inner envelope 14 contained within the outer envelope 16 but forming a distinct, fluidly separated container there from. The inner envelope 14 may be of the same general shape as the outer envelope 16 or may be spherical, ovoid or otherwise elongate. The walls of the inner envelope 14 may be made of the same or similar materials as the outer walls 16 described above. The inner envelope 14 may be adjacent to and affixed to one or more walls of the outer envelope 14 (as in FIG. 10), generally centered and affixed within the volume of the outer envelope (as in FIG. 9) or free floating (i.e. unattached) within the outer envelope. Tubular member 8 may extend into the volume of the outer envelope 16 to fluidly engage the inner envelope 14, as in FIG. 9 for example. Alternately, tubular member 8 may, as noted, be comprised of multiple lumens such that one lumen fluidly engages the outer envelope 16 while another lumen engages the inner envelope 14, as in FIG. 11 for example. In such an embodiment a second fill port (not shown) may be provided at the anchor member 2 in fluid engagement with the additional lumen of the tubular member 8. Alternately, in an embodiment such as depicted in FIG. 5, one of either the inner or outer envelopes 14, 16 may be filled to a fixed volume by a single use port (not shown) during implantation with only the single lumen in fluid contact with the tubular member 8 and port 6 for subsequent filling or evacuation as described below.

In use the spacer is implanted in a mini-open procedure in which the interspinous ligament is resected and the anchor member positioned within the interspinous space. The deflated expandable/collapsible member 10 is preferably secured in position prior to implantation and is most preferably inside the wedge formed by the bridging member and base member. The arcuate base member provides an initial amount of distraction with direct contact to the spinous processes after the wedge is worked into place. When positioned to the surgeon's satisfaction, bone screws 28 are driven through slots 30 at or near the apex of the inferior and superior spinous processes to secure the spacer 1 in position. Where a single envelope expandable/collapsible member 10 is utilized the member is then expanded to an initial position to distract the vertebra by filling with a flowable material 22 to increase the envelope volume and achieve the desired dimensions and distraction. A maximum distraction of approximately 20 mm can be achieved by the fully inflated expandable member. Expansion of a two envelope member 10 is accomplished by filling the inner and/or outer envelopes with a flowable material 22 to increase the envelope volume and achieve the desired dimensions and distraction as described above. After a satisfactory level of initial distraction is achieved at the discretion of the surgeon the patient is closed and the incision allowed to heal. Subsequent to the initial implantation the volume of the expandable/collapsible member 10 can be adjusted during an in-office non-surgical procedure to add or remove fluid from the outer envelope 16. Addition or subtraction of fluid is accomplished by locating the position of the subcutaneous port 6 of the patient and insertion of a needle into the port through the skin. Increasing the volume of fluid within the envelope 16 increases the distraction of the joint while decreasing the volume has the opposite effect.

The flowable material 22 may be a sterile saline solution, silicone oil or gel, urethane or other viscous polymer. In certain embodiments the flowable material may be a two-part polymer such a two-part urethane such that the initial fill and distraction of the vertebral joint is accomplished by filling with a first part in flowable form. Subsequently, after the volume of the expandable/collapsible member 10 has been adjusted to a final position through the above described in-office procedure the second part of the two-part polymer may be injected by needle insertion into port 6 causing a reaction that hardens the polymer into a non-flowing elastomeric compound suitable for long term in-situ use.

In an alternate embodiment in which the expandable/collapsible member 10 is comprised of an inner envelope 14 and an outer envelope 16, the spacer 1 is implanted as described. After implantation one of the envelopes, preferably outer envelope 16 is expanded by introduction of a flowable material 22 via a port to produce an initial distraction as described in the single envelope case. In such an alternate embodiment flowable material 22 may be a viscous fluid and may further harden to an elastomeric solid without further intervention such as the introduction of a "hardener." Inner envelope 14 may be minimally expanded by introduction of a fluid via port 6 or may remain evacuated. After the procedure is completed the patient may, as described above, return to the physician for a non-surgical in-office procedure in which flowable material 22 is added or removed from the inner envelope 14 to adjust the volume of the expandable/collapsible member 10 and thus adjust the level of distraction. The flowable material introduced into the inner envelope 14 may be the same material introduced into the outer envelope 16 or may be a different material with different flow characteristics and/or hardening properties.

It should be understood that the disclosure of this may be used with a variety of interspinous process spacer forms and designs. It should also be understood that the disclosure may be constructed of a variety of suitable surgical grade materials including stainless steel and titanium as well as composite materials having suitable strength and corrosion resistance properties should such materials be approved for surgical implantation. This application is therefore intended to cover any variations, uses, or adaptations of the invention using its general principles. Further, this application is intended to cover such departures from the present disclosure as come within known or customary practice in the art to which this invention pertains.

I claim:

1. A dynamic spacer for insertion between the spinous processes of a superior and inferior vertebra of a spine having a longitudinal axis, comprising:
    a rigid anchor member for engaging a surface of each of said spinous processes, said anchor member comprising a web, and two legs fixedly engaged to and extending orthogonally from said web to form a channel having a longitudinal axis aligned with said longitudinal axis of said spine, each said two legs having a first slot in a first end operatively positioned for sliding engagement with said superior vertebra along said longitudinal axis of said spine and a second slot in a second end operatively positioned for sliding engagement with said inferior vertebra along said longitudinal axis of said spine;
    a bridging member engaged between a distal end of a first of said two legs and a distal end of a second of said two legs;
    in each of said first and second slots, a fastener slideably engaged with one of said slots for fixed engagement with one of said vertebra;
    a port for receiving fluid;
    an outer expandable envelope affixed to said anchor member and in fluid engagement with said port, said outer expandable envelope inflatable by a fluid introduced via said port to engage and distract said superior and inferior vertebra;
    wherein said bridging member is shorter in the direction of said longitudinal axis than said web and cooperatively formed therewith to together define a wedge.

2. The dynamic spacer of claim 1 further comprising a tubular member extending from said port in fluid engagement with said port at a first end and with said outer expandable envelope at a second end.

3. The dynamic spacer of claim 1 wherein said web is arcuate.

4. The dynamic spacer of claim 1 wherein said channel is arcuate.

5. The dynamic spacer of claim 1 wherein each of said two legs are splayed.

6. The dynamic spacer of claim 5 wherein each of said two legs are splayed at an angle of from 5° to 15°.

7. The dynamic spacer of claim 1 wherein said outer expandable envelope is affixed within said channel.

8. The dynamic spacer of claim 1 wherein said outer expandable envelope is affixed to said bridging member.

9. The dynamic spacer of claim 1 wherein said outer expandable envelope when expanded fills said channel so as to abut said web and said legs.

10. A dynamic spacer for insertion between the spinous processes of a superior and inferior vertebra of a spine having a longitudinal axis, comprising:
    a rigid anchor member for engaging a surface of each of said spinous processes, said anchor member comprising a web, and at least one leg fixedly engaged to and extending orthogonally from said web, each said at least one leg having a first slot in a first end operatively positioned for sliding engagement with said superior vertebra along said longitudinal axis of said spine and a second slot in a second end operatively positioned for sliding engagement with said inferior vertebra along said longitudinal axis of said spine;
    in each of said first and second slots, a bone screw slideably engaged with one of said slots for fixed engagement with one of said vertebra, each said bone screw having a head with an annular channel around said heads of said bone screws, said leg being received within said channels;
    a port for receiving fluid;
    an outer expandable envelope affixed to said anchor member and in fluid engagement with said port, said outer expandable envelope inflatable by a fluid introduced via said port to engage and distract said superior and inferior vertebra.

11. A dynamic spacer for insertion between the spinous processes of a superior and inferior vertebra of a spine having a longitudinal axis, comprising:
    a rigid anchor member for engaging a surface of each of said spinous processes, said anchor member comprising a web, and at least one leg fixedly engaged to and extending orthogonally from said web, each said at least one leg having a first slot in a first end operatively positioned for sliding engagement with said superior vertebra along said longitudinal axis of said spine and a second slot in a second end operatively positioned for sliding engagement with said inferior vertebra along said longitudinal axis of said spine;
    in each of said first and second slots, a bone screw slideably engaged with one of said slots for fixed engagement with one of said vertebra, each said bone screw comprises a head, and a spacer portion having a diameter greater than a major diameter of said screw below said head whereby said screw head is held above a surface of one of said vertebra when said screw is implanted in said vertebra;
    a port for receiving fluid;
    an outer expandable envelope affixed to said anchor member and in fluid engagement with said port, said outer expandable envelope inflatable by a fluid introduced via said port to engage and distract said superior and inferior vertebra.

* * * * *